(12) United States Patent
Lubisch et al.

(10) Patent No.: US 6,509,365 B1
(45) Date of Patent: Jan. 21, 2003

(54) 2-PHENYLBENZIMIDAZOLES AND 2-PHENYLINDOLES, AND PRODUCTION AND USE THEREOF

(75) Inventors: Wilfried Lubisch, Heidelberg (DE); Michael Kock, Schifferstadt (DE); Thomas Höger, Edingen-Neckarhausen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,036

(22) PCT Filed: Nov. 5, 1999

(86) PCT No.: PCT/EP99/08466
§ 371 (c)(1),
(2), (4) Date: May 17, 2001

(87) PCT Pub. No.: WO00/29384
PCT Pub. Date: May 25, 2000

(30) Foreign Application Priority Data

Nov. 17, 1998 (DE) .......................... 198 52 816

(51) Int. Cl.$^7$ .................. C07D 235/04; A61K 31/4184
(52) U.S. Cl. ..................... 514/393; 548/309.7
(58) Field of Search .......... 548/309.7, 310.1, 548/310.4, 310.7; 514/393

(56) References Cited

U.S. PATENT DOCUMENTS 5,395,840 A * 3/1995 Müller et al. ............... 514/300

FOREIGN PATENT DOCUMENTS

| WO | 97/04771 | * | 2/1997 |
| WO | 98/06703 | * | 2/1998 |

* cited by examiner

Primary Examiner—Joseph K. McKane
Assistant Examiner—Golam M M Shameem
(74) Attorney, Agent, or Firm—Keil & Weinkauf

(57) ABSTRACT

2-Phenylbenzimidazoles and 2-phenylindoles of formula I

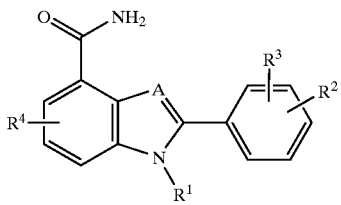

I wherein
A is N or CH,
$R^1$ is hydrogen or alkyl which optionally carries an $OR^{11}$ group,
$R^{11}$ is hydrogen or alkyl,
$R^2$ is hydrogen, chlorine, fluorine, bromine, iodine, alkyl, nitro, $CF_3$, CN, $NR^{21}R^{22}$, NH—CO—$R^{23}$, $OR^{21}$,
$R^{21}$ and $R^{22}$ are each hydrogen or alkyl,
$R^{23}$ is hydrogen, alkyl or phenyl,
$R^3$ is —$(CH_2)_q$—$NR^{31}R^{32}$,
q is 0, 1, 2 or 3,
$R^{31}$ is hydrogen, alkyl, $(CH_2)_rNR^{33}R^{34}$,
$R^{32}$ is $(CH_2)_rNR^{33}R^{34}$,
r is 2, 3, 4, 5 or 6,
$R^{33}$ and $R^{34}$ are each hydrogen, alkyl or phenylalkyl wherein the phenyl ring is optionally substituted, or
$R^{33}$ and $R^{34}$ and the nitrogen atom form a 3- to 8-membered ring,
$R^4$ is hydrogen, alkyl, chlorine, bromine, fluorine, nitro, cyano, $NR^{41}R^{42}$, NH—CO—$R^{43}$, $OR^{41}$,
$R^{41}$ and $R^{42}$ are each hydrogen or alkyl, and
$R^{43}$ is alkyl or phenyl,
are useful as inhibitors of poly(ADP-ribose)polymerase and for the production of drugs.

22 Claims, No Drawings

2-PHENYLBENZIMIDAZOLES AND 2-PHENYLINDOLES, AND PRODUCTION AND USE THEREOF

This application is a 371 of PCT/EP 99/08466 filed Nov. 5, 1999.

The present invention relates to novel 2-phenylbenzimidazoles and 2-phenylindoles, their preparation and their use as inhibitors of the enzyme poly(ADP-ribose)polymerase or PARP (EC 2.4.2.30) for the production of drugs.

Poly(ADP-ribose)polymerase (PARP) or poly(ADP-ribose)synthase (PARS), as it is also known, is a regulatory enzyme which is found in cell nuclei (K. Ikai et al., *J. Histochem. Cytochem.* 1983, 31, 1261–1264). It is assumed that PARP plays a part in the repair of DNA bridges (M. S. Satoh et al., *Nature* 1992, 356, 356–358). Damage to or breaks in the DNA strands activate the enzyme PARP which, when it is activated, catalyzes the conversion of ADP-ribose from NAD (S. Shaw, *Adv. Radiat. Biol.,* 1984, 11, 1–69). During the course of this, nicotinamide is released from NAD. Nicotinamide is converted into NAD again with consumption of the energy carrier ATP of other enzymes. Overactivation of PARP would accordingly have resulted in an unphysiologically high consumption of ATP and this leads, in extreme cases, to cell damage and cell death.

It is known that free radicals such as the superoxide anion, NO and hydrogen peroxide can lead to DNA damage in cells and thus activate PARP. The formation of large amounts of free radicals is observed in a number of pathophysiological conditions and it is assumed from this that this accumulation of free radicals leads or contributes to the observed cell and organ damage. This includes, for example, ischemic conditions of organs such as in stroke, cardiac infarct (C. Thiemermann et al., *Proc. Natl. Acad. Sci. USA,* 1997, 94, 679–683) or ischemia of the kidneys, but also reperfusion damage such as occurs, for example, after lysis of cardiac infarct (see above: C. Thiemermann et al.). The inhibition of the enzyme PARP could accordingly be a means of preventing or alleviating this damage at least partly. PARP inhibitors could thus be a new therapeutic principle for the treatment of a number of diseases.

The enzyme PARP affects the repair of DNA damage and could thus also play a part in the therapy of carcinomatous disorders, since in combination with cytostatically active substances a higher potential of action against tumor tissue was observed (G. Chen et al. *Cancer Chemo. Pharmacol.* 1988, 22, 303).

Nonlimiting examples of tumors are leukemia, glioblastoma, lymphoma, melanoma, mastocarcinoma and cervical carcinoma.

Moreover, it has been found that PARP inhibitors can show immunosuppressant action (D. Weltin et al. *Int. J. Immunopharmacol.* 1995, 17, 265–271).

It was also discovered that PARP is involved in immunological disorders or diseases in which the immune system plays an important part, such as, for example, rheumatoid arthritis and septic shock, and that PARP inhibitors can show a favorable effect on the course of the disease (H. Kröger et al. *Inflammation* 1996, 20, 203–215; W. Ehrlich et al. *Rheumatol. Int.* 1995, 15, 171–172; C. Szabo et al., *Proc. Natl. Acad. Sci. USA* 1998, 95, 3867–3872; S. Cuzzocrea et al. *Eur. J. Pharmacol.* 1998, 342, 67–76).

Within the meaning of this invention, PARP is understood as also meaning isoenzymes of the above-described PARP enzyme.

Furthermore, the PARP inhibitor 3-aminobenzamide showed protective effects in a model for circulatory shock (S. Cuzzocrea et al., *Br. J. Pharmacol.* 1997, 121, 1065–1074).

There are likewise experimental indications that inhibitors of the enzyme PARP could be useful as an agent for the treatment of diabetes mellitus (V. Burkart et al. *Nature Med.* 1999, 5, 314–319).

2-Phenylbenzimidazoles have been widely described. Thus, in DE 38 30 060 alkylated derivatives are disclosed as inhibitors of erythrocyte aggregation. In DE 35 22 230, an ester derivative of 2-phenylbenzimidazole is mentioned as an inhibitor of platelet aggregation. Halogen-substituted 2-phenylbenzimidazoles which carry substituted amine radicals on the phenyl ring have been described as MCP-1 antagonists in WO 98/06703.

2-Phenylbenzimidazoles are also known in which the benzimidazole group is substituted by an amide group. 5-Amido derivatives of 2-phenylbenzimidazole, which carry alkyloxy radicals on the phenyl ring, have been described as inhibitors of cAMP phosphodiesterase in WO 94/12461. For analogous derivatives, it was found in DE 35 46 575 (e.g. Example 15) that these compounds induce positively inotropic effects. 4-Amido derivatives which carry a pyridyl radical in the 3-position are also described as inhibitors of cAMP phosphodiesterase in WO 97/48697.

The synthesis of 2-phenylbenzimidazyl-4-amides has been described in J. Chem. Soc. Perkin Trans 1, 1979, 2303–2307. Analogous compounds which carry a further substituted alkyl chain on the amide radical, and which are said to have cytotoxic action, are mentioned in J. Med. Chem. 1990, 33, 814–819. In WO 97/04771, however, benzimidazole-4-amides which inhibit PARS are mentioned. In particular, derivatives which carry a phenyl ring in the 2-position are described as active there, it additionally being possible to substitute the phenyl ring with simple substituents such as nitro, methoxy and $CF_3$. Although these substances in some cases show good inhibition of the enzyme PARP, the derivatives described there have the disadvantage that they only show little or no solubility in aqueous solutions and thus cannot be administered as an aqueous solution.

In a number of therapies such as stroke, the active compounds are administered intravenously as an infusion solution. To this end, it is necessary to have available substances, in this case PARP inhibitors, which have sufficient water solubility at physiological pHs or approximate pHs (e.g.: pHs of 5–8) so that an infusion solution can be prepared. Many of the described PARP inhibitors, in particular the better active PARP inhibitors, have the disadvantage, however, that they only show low or no water solubility at these pHs and are thus not suitable for intravenous administration. Active compounds of this type can only be administered with auxiliaries which are intended to mediate the water solubility (cf. WO 97/04771). These auxiliaries, for example polyethylene glycol and dimethyl sulfoxide, often cause side effects or are even intolerable. Highly efficacious PARP inhibitors having adequate water solubility have not been described until now.

It has surprisingly been found that 2-phenylbenzimidazoles which additionally carry an amine radical on the phenyl ring are highly efficacious inhibitors which, however, make possible salt formation with acids due to the incorporation of the aliphatic amine radical and as a result show a markedly improved water solubility.

In the present invention, novel 2-phenylbenzimidazole and 2-phenylindole derivatives of the general formula I are described which, compared with the compounds already described, show advantages and are potent PARP inhibitors and at the same time also show adequate water solubility, which makes possible administration as an infusion solution.

The present invention relates to substituted 2-phenylbenzimidazoles and 2-phenylindoles of the general formula I:

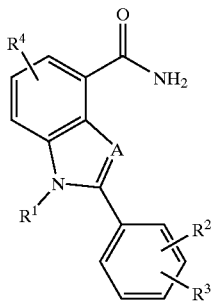

in which

A is N or CH,

R$^1$ is hydrogen, branched or unbranched C$_1$–C$_6$-alkyl, where one C atom of the alkyl radical can further carry OR$^{11}$, where
R$^{11}$ is hydrogen or C$_1$–C$_4$-alkyl, and R$^2$ is hydrogen, chlorine, fluorine, bromine, iodine, branched or unbranched C$_1$–C$_6$-alkyl, nitro, CF$_3$, CN, NR$^{21}$R$^{22}$, NH—CO—R$^{23}$, OR$^{21}$, where
R$^{21}$ and R$^{22}$ independently of one another are hydrogen or C$_1$–C$_4$-alkyl and
R$^{23}$ is hydrogen, C$_1$–C$_4$-alkyl or phenyl, and R$^3$ is —(CH$_2$)$_q$—NR$^{31}$R$^{32}$, (CH$_2$)$_q$—NR$^{33}$R$^{34}$, where q can be 0, 1, 2 or 3
R$^{31}$ is hydrogen, C$_1$–C$_6$-alkyl, (CH$_2$)$_4$NR$^{33}$R$^{34}$,
R$^{32}$ is (CH$_2$)$_r$NR$^{33}$R$^{34}$, in which, if R$^{31}$ and R$^{32}$ are independent of one another, r is 2, 3, 4, 5 or 6 and R$^{33}$ and R$^{34}$ independently of one another are hydrogen, C$_1$–C$_6$-alkyl, together with the nitrogen atom are a ring of 3 to 8 atoms which can carry an additional heteroatom selected from O, N—C$_1$–C$_4$-alkyl, N—C$_0$–C$_2$-phenyl or NH, phenyl-C$_1$–C$_4$-alkyl, where the phenyl ring can be substituted by up to 3 identical or different subtituents selected from the group consisting of C$_1$–C$_6$-alkyl, halogen, nitro, SO$_2$NR$^{35}$R$^{36}$ (where R$^{35}$, R$^{36}$ independently of one another are hydrogen, C$_1$–C$_4$-alkyl or together with the nitrogen are a ring of 3 to 8 atoms which can carry an additional hetero atom selected from O, S, SO$_2$, N—C$_1$–C$_4$-alkyl, N—C$_0$–C$_2$-phenyl or NH), C$_1$–C$_4$-alkoxy, S(O)$_{0-2}$—R$^{37}$ (where R$^{37}$ is hydrogen, C$_1$–C$_4$-alkyl), CF$_3$, (CH$_2$)$_{0-4}$—COR$^{37}$, (CH$_2$)$_{0-4}$NR$^{35}$R$^{36}$, (CH$_2$)$_{0-4}$CONR$^{35}$R$^{36}$, (CH$_2$)$_{0-4}$OR$^{37}$—CH$_2$COOR$^{37}$, R$^4$ is hydrogen, branched or unbranched C$_1$–C$_6$-alkyl, chlorine, bromine, fluorine, nitro, cyano, NR$^{41}$R$^{42}$, NH—CO—R$^{43}$, OR$^{41}$, where R$^{41}$ and R$^{42}$ independently of one another are hydrogen or C$_1$–C$_4$-alkyl and
R$^{43}$ is C$_1$–C$_4$-alkyl or phenyl.

Preferred positions for the radical R$^2$ in the general formula I are the 3-position and the 4-position relative to the benzimidazole ring. For the radical R$^3$, the 3-position or 4-position relative to the benzimidazole ring is likewise preferred.

The preferred meaning of A is nitrogen.

The preferred meaning of R$^1$ is hydrogen.

The preferred meaning of R$^2$ is hydrogen, branched or unbranched C$_1$–C$_6$-alkyl, nitro, CN, NH$_2$, O—C$_1$–C$_4$-alkyl. R$^2$ is particularly preferably hydrogen.

The preferred meaning of R$^3$ is (CH$_2$)$_{1-2}$—NR$^{33}$R$^{34}$ and N(R$^{31}$)—(CH$_2$)$_{2-3}$—NR$^{33}$R$^{34}$, in which R$^{31}$ is hydrogen or C$_1$–C$_4$-alkyl, R$^{33}$ and R$^{34}$ independently of one another are hydrogen or C$_1$–C$_4$-alkyl, or the group NR$^{33}$R$^{34}$ represents a radical selected from the group consisting of piperidine, pyrrolidine, azepine and piperazine, where the piperazine on the second N is substituted by hydrogen or C$_1$–C$_4$-alkyl.

The preferred meaning of R$^4$ is hydrogen.

The respective combinations of the above preferred meanings are very particularly preferred.

The compounds of the formula I can be employed as racemates, as enantiomerically pure compounds or as diastereomers. If enantiomerically pure compounds are desired, these can be obtained, for example, by carrying out a classical resolution with the compounds of the formula I or their intermediates using a suitable optically active base or acid.

The invention also relates to compounds which are mesomeric or tautomeric to compounds of the formula I.

The invention further relates to the physiologically tolerable salts of the compounds I which can be obtained by reaction of compounds I with a suitable acid or base. Suitable acids and bases are listed, for example, in Fortschritte der Arzneimittelforschung, 1966, Birkhäuser Verlag, Vol. 10, pp. 224–285. These include, for example, hydrochloric acid, citric acid, tartaric acid, lactic acid, phosphoric acid, methanesulfonic acid, acetic acid, formic acid, maleic acid, fumaric acid etc., and sodium hydroxide, lithium hydroxide, potassium hydroxide and tris.

Prodrugs are understood as meaning those compounds which are metabolized to compounds of the general formula I in vivo. Typical produgs are phosphates, carbamates of amino acids, esters and others.

The preparation of the substances I according to the invention can be carried out in various ways, which are analogous to those which have been outlined in WO 98/06703 for benzimidazole and indole, and Synthesis Schemes 1–3.

Synthesis Scheme 1

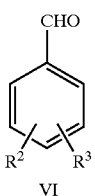

VI

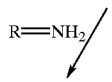

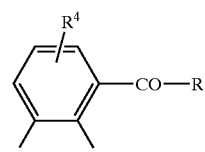

VII

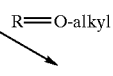

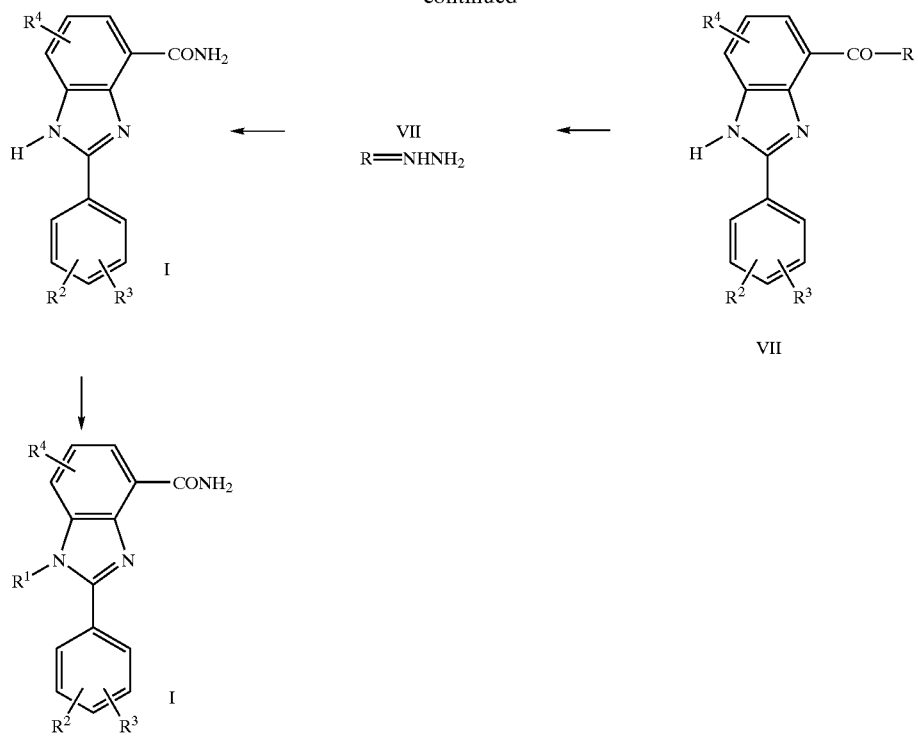

The benzimidazole VII is obtained by condensation of the benzaldehyde with phenylenediamines, the reaction preferably being carried out in polar solvents such as ethanol or dimethylformamide and with addition of acids such as acetic acid at elevated temperature, as a rule 80–120° C. The addition of weak oxidants such as copper(II) salts, which are added as an aqueous solution, is favorable for the reaction.

Synthesis Scheme 2

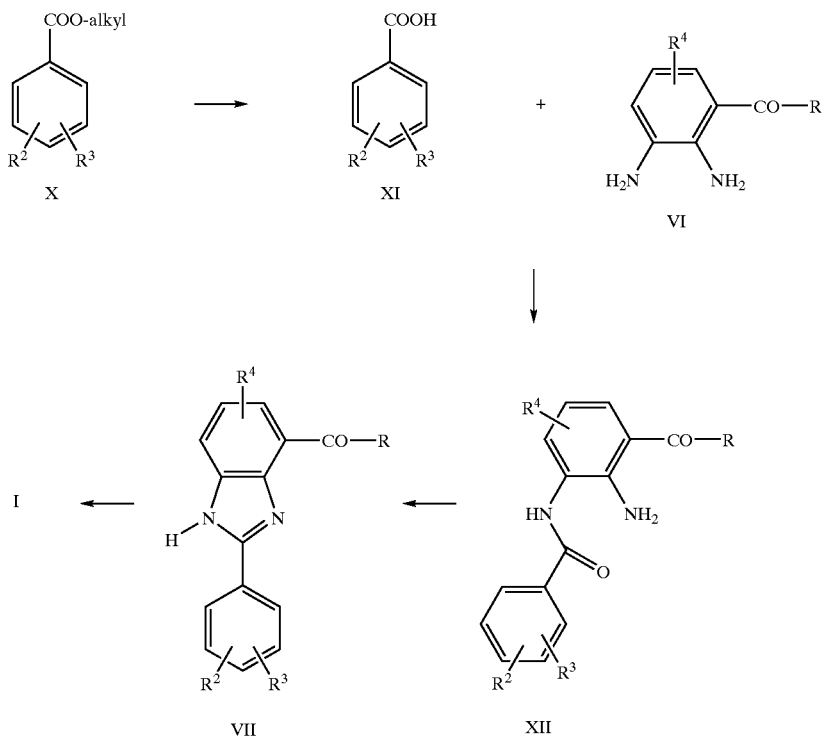

If R=NH$_2$ in the phenylenediamine VII, compounds I according to the invention are formed directly in the condensation. Otherwise, if R=O-alkyl, this ester can be reacted with ammonia, if appropriate at elevated temperature and elevated pressure, to give the amide I. Alternatively, the ester VII can be reacted with hydrazine in polar solvents such as the alcohols butanol and ethanol or alternatively dimethylformamide, at elevated temperatures, preferably 80–130° C., a hydrazide VII (R=NHNH$_2$) being obtained which can then additionally be reduced under reductive conditions, such as with Raney nickel in alcohols under reflux, to give the amide I.

Introduction of the radical R$^1$ into the benzimidazole radical in I (R$^1$=H) takes place under alkylating conditions as above (see V–VI), where, however, the reaction component R$^1$—L (L=leaving group as above) has to be employed (see Scheme 1).

ditions. The reaction can in this case be carried out in solvents such. as dimethylformamide with addition of acids or also in polyphosphonic acid at elevated temperature such as 60–200° C. However, the customary methods for the preparation of amidines from benzonitriles can also be used, such as are described in Houben-Weyl, Methoden der Organischen Chemie (Methods of Organic Chemistry), E5, p.1304 f., J. Amer. Chem. Soc. 1957, 427 and J. Org. Chem. 1987, 1017.

The substituted 2-phenylbenzimidazoles and 2-phenylindoles I contained in the present invention are inhibitors of the enzyme poly(ADP-ribose)polymerase or PARP (EC 2.4.2.30).

The inhibitory action of the substituted 2-phenylbenzimidazoles and 2-phenylindoles I was determined using an enzyme test already known in the literature, a K$_i$ value being determined as an activity standard. The Synthesis Scheme 3

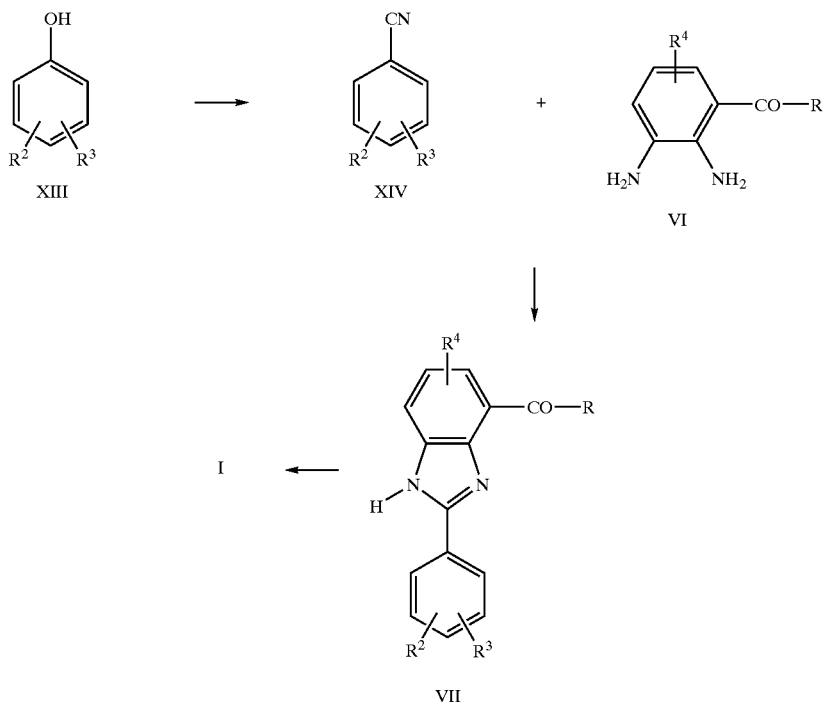

Alternatively to the benzaldehydes VI shown in Scheme 1, benzoic acids such as XI (see Scheme 2) or benzonitriles such as XIV (see Scheme 3) can be employed instead of the benzaldehyde. The preparation of these derivatives is carried out analogously to the preparation of the substituted benzaldehydes V. Starting from XI, the condensation to give VII is carried out in two stages. First, the benzoic acid XI is reacted with the aniline VI in a peptide-like coupling to give the amide XII. The reaction here is carried out according to customary conditions, which are listed, for example, in Houben-Weyl, Methoden der Organischen Chemie (Methods of Organic Chemistry), 4$^{th}$ Ed., E5, Chap. V or C. R. Larock, Comprehensive Organic Transformations, VCH Publisher, 1989, page 972 ff. The ring closure to give the benzimidazole is then carried out at elevated temperature, for example 60–180° C., with or without solvents such as dimethylformamide, with addition of acids such as acetic acid or directly in acetic acid itself.

The reaction of the phenylenediamine VII with a benzonitrile XIV is likewise carried out under customary con- 2-phenylbenzimidazoles and 2-phenylindoles I were measured in this manner for inhibitory action of the enzyme poly(ADP-ribose)polymerase or PARP (EC 2.4.2.30).

The substituted 2-phenylbenzimidazoles and 2-phenylindoles of the general formula I are inhibitors of poly(ADP-ribose)polymerase (PARP) or poly(ADP-ribose) synthase (PARS) as it is also called and can thus be used for the treatment and prophylaxis of diseases which are associated with an increased enzyme activity of these enzymes.

The compounds of the formula I can be employed for the production of drugs for the treatment of damage after ischemia and for prophylaxis in the case of expected ischemias of various organs.

The present 2-phenylbenzimidazoles and 2-phenylindoles of the general formula I can accordingly be used for the treatment and prophylaxis of neurodegenerative diseases which occur after ischemia, trauma (craniocerebral trauma), mass hemorrhages, subarachnoid hemorrhages and stroke, and of neurodegenerative diseases such as multiple infarct dementia, Alzheimer's disease, Huntington's disease and of epilepsies, in particular of generalized epileptic attacks, such as, for example, petit mal and tonic-clonic attacks and partial epileptic attacks, such as temporal lobe and complex partial attacks, and furthermore for the treatment and prophylaxis of damage to the heart after cardiac ischemia and damage to the kidneys after renal ischemia, for example of acute renal insufficiency, of acute kidney failure or of damage which occurs during and after a kidney transplant. The compounds of the general formula I can furthermore be used for the treatment of acute myocardial infarct and damage which occurs during and after medicinal lysis thereof (for example with TPA, reteplase, streptokinase or mechanically with a laser or Rotablator) and of microinfarcts during and after heart valve replacement, aneurysm resections and heart transplants. The present 2-phenylbenzimidazoles and 2-phenylindoles I can likewise be used for the treatment of revascularization of critically constricted coronary arteries, for example in PCTA and bypass operations, and critically constricted peripheral arteries, for example leg arteries. Moreover, the 2-phenylbenzimidazoles and 2-phenylindoles I can be beneficial in the chemotherapy of tumors and metastasis thereof and can be used for the treatment of inflammation and rheumatic disorders, such as, for example, rheumatoid arthritis.

In addition to the customary pharmaceutical auxiliaries, the pharmaceutical preparations according to the invention contain a therapeutically efficacious amount of the compounds I.

For local external application, for example in powders, ointments or sprays, the active compounds can be contained in the customary concentrations. As a rule, the active compounds are contained in an amount of 0.001 to 1% by weight, preferably 0.001 to 0.1% by weight.

In the case of internal administration, the preparations are administered in individual doses. In an individual dose, 0.1 to 100 mg are provided per kg of body weight. The preparations can be administered daily in one or more doses depending on the nature and severity of the disorders.

According to the type of administration desired, the pharmaceutical preparations according to the invention contain the customary carriers and diluents in addition to the active compound. For local external application, industrial pharmaceutical auxiliaries, such as ethanol, isopropanol, ethoxylated castor oil, ethoxylated hydrogenated castor oil, polyacrylic acid, polyethylene glycol, polyethylene glycol stearate, ethoxylated fatty alcohols, paraffin oil, petroleum jelly and wool fat can be used. For internal administration, for example, lactose, propylene glycol, ethanol, starch, talc and polyvinylpyrrolidone are suitable.

Antioxidants such as tocopherol and butylated hydroxyanisole and also butylated hydroxytoluene, flavor-enhancing additives, stabilizers, emulsifiers and lubricants can furthermore be contained.

The substances contained in addition to the active compound in the preparation and the substances used in the production of pharmaceutical preparations are toxicologically acceptable and compatible with the respective active compound. The production of the pharmaceutical preparations is carried out in a customary manner, for example by mixing the active compound with other customary carriers and diluents.

The pharmaceutical preparations can be administered in various manners of administration, for example orally, parenterally, such as intravenously by infusion, subcutaneously, intraperitoneally and topically. Thus preparation forms such as tablets, emulsions, infusion and injection solutions, pastes, ointments, gels, creams, lotions, powders and sprays are possible.

EXAMPLE 1

2-(4-(N,N-2-(N,N-Diethylamino)eth-1-ylmethylamino)phenyl)benzimidazole-4-carboxamide a) Ethyl 2-(4-(N,N-2-(N,N-diethylamino)eth-1-ylmethylamino)phenyl)benzimidazole-4-carboxylate 2.0 g (12 mmol) of ethyl 2,3-diaminobenzoate were dissolved in 100 ml of methanol and mixed with 1.7 ml (27.7 mmol) of acetic acid. 2.4 g (10.1 mmol) of 4-(2-(N,N-diethylamino)eth-1-ylmethylamino)benzaldehyde, dissolved in 100 ml of methanol, were then added dropwise in the course of 30 minutes. A solution of 1.7 g (8.5 mmol) of copper(II) acetate in 30 ml of water was then added dropwise and then everything was heated under reflux for 50 minutes. The reaction solution was allowed to cool to 50° C. and 20 ml of 32% strength hydrochloric acid were carefully added. A solution of 3.9 g (16.2 mmol) of sodium sulfide hydrate in 20 ml of water was then also added dropwise and everything was stirred for 10 minutes. The precipitate was filtered off with suction and the filtrate was rendered alkaline by addition of aqueous sodium hydrogencarbonate solution. This aqueous phase was extracted with ethyl acetate, and the organic phase was separated off, dried and concentrated in vacuo. 2.6 g of the product were obtained.

b) 2-(4-(N,N-2-(N,N-Diethylamino)eth-1-ylmethylamino)phenyl)benzimidazole-4-carbohydrazide 2.6 g (6.8 mmol) of the intermediate 1 and 3.4 g (68.3 mmol) of hydrazine hydrate were added to 70 ml of n-butanol and the mixture was heated at 120° C. for 12 hours. The butanol was then removed in vacuo. The residue obtained was partitioned between water and ethyl acetate. The organic phase was separated off, dried and concentrated in vacuo. 1.1 g of the product were obtained.

c) 2-(4-(N,N-2-(N,N-Diethylamino)eth-1-ylmethylamino)phenyl)benzimidazole-4-carboxamide 1 g of Raney nickel was added to 1.1 g (2.9 mmol) of the intermediate 1b in 30 ml of dimethylformamide and everything was heated at 120° C. for 8 hours. The reaction mixture was filtered and the filtrate was concentrated in vacuo. The residue obtained was partitioned between water and ethyl acetate. The organic phase was separated off, dried and concentrated in vacuo. 0.9 g of the product was obtained. $^1$H-NMR(D$_6$-DMSO): δ=2.2 (6H), 2.4 (2H), 3.0 (3H), 3.5 (2H), 6.8 (2H), 7.2 (1H), 7.6–7.8 (3H), 8.1 (2H), 9.5 (1H) and 13.2 (1H) ppm.

EXAMPLE 2

2-(4-(N,N-2-(N,N-Dimethylamino)eth-1-ylmethylamino)phenyl)benzimidazole-4-carboxamide The compound was prepared analogously to the procedures in Example 1 $^1$H-NMR(D$_6$-DMSO): δ=2.2 (6H), 2.55 (2H), 3.1 (2H), 7.4 (1H), 7.8 (2H), 7.9 (1H), 8.1 (1H), 8.3 (1H), 8.4 (1H), 9.2 (1H) ppm.

EXAMPLE 3

2-(3-(2-(N,N-Dimethylamino)eth-1-yl)-4-nitrophenyl)benzimidazole-4-carboxamide a) Methyl 3-(E-2-N,N-dimethylaminoethen-1-yl)-4-nitrobenzoate 10 g (47.8 mmol) of ethyl 3-methyl-4-nitrobenzoate and 30 ml of N,N-dimethylformamide dimethyl acetal were refluxed for 8 hours in 100 ml of dimethylformamide. The mixture was then concentrated in vacuo. The residue was dissolved in 100 ml of toluene and the product was precipitated by addition of petroleum ether. 7.5 g of the product were obtained.

b) 3-(2-N,N-Dimethylaminoeth-1-yl)-4-nitrobenzyl alcohol 2.0 g (53 mmol) of sodium borohydride were added in portions to 7 g (26.5 mmol) of the intermediate 3a in 70 ml of ethanol. Everything was then heated under reflux for 30 minutes. The reaction solution was then concentrated in vacuo. The residue obtained was partitioned between water and ethyl acetate. The organic phase was separated off, washed with water and with aqueous sodium chloride solution, dried and concentrated in vacuo. The oil thus obtained was dissolved in ethanol and treated with ethereal hydrogen chloride solution. The product crystallized as the hydrochloride. 2.5 g were obtained.

c) 3-(2-N,N-Dimethylaminoeth-1-yl)-4-nitrobenzaldehyde 2.35 g (9 mmol) of the intermediate 3b and 6.3 ml (45 mmol) of triethylamine were dissolved in 50 ml of dimethyl sulfoxide. 2.9 g (18 mmol) of the pyridine-sulfur trioxide adduct were then added in portions and everything was stirred for 60 minutes. The mixture was then concentrated in vacuo and the residue was partitioned between water and ethyl acetate. The organic phase was washed a further two times with water, dried and concentrated in vacuo. 1.8 g of the product were obtained.

d) 2-(3-(2-(N,N-dimethylamino)eth-1-yl)-4-nitrophenyl)benzimidazole-4-carboxamide The intermediate 3c was reacted to give the product analogously to the procedures of Example 1a, b and c. $^1$H-NMR (D$_6$-DMSO): δ=1.25 (6H), 3.1 (3H), 3.2 (4H), 3.9 (2H), 7.0 (2H), 7.2 (1H), 7.6–7.9 (3H), 8.1 (2H), 9.5 (1H), 10.9 (1H) and 13.5 (broad) ppm.

The following examples can be prepared analogously to the methods which were described in WO 98/06703 or to the methods which are described in the present application:

1. 2-(4-(Dimethylamino)methyl)phenylbenzimidazole-4-carboxamide
2. 2-(4-(Dimethylamino)methyl)phenylbenzimidazole-4-carboxamide
3. 2-(4-(Pyrrolidin-1-yl)methyl)phenylbenzimidazole-4-carboxamide
4. 2-(4-(Piperidin-1-yl)methyl)phenylbenzimidazole-4-carboxamide
5. 2-(4-Aminomethyl)phenylbenzimidazole-4-carboxamide
6. 2-(4-(Methylaminio)methyl)phenylbenzimidazole-4-carboxamide
7. 2-(4-(Propylamino)methylphenylbenzimidazole-4-carboxamide
8. 2-(4-(2-(Diethylamino)eth-1-yl)phenyl)benzimidazole-4-carboxamide
9. 2-(4-(2-(Dimethylamino)eth-1-yl)phenyl)benzimidazole-4-carboxamide
10. 2-(4-(2-Aminoeth-1-yl)phenyl)benzimidazole-4-carboxamide
11. 1-(2-(2-(Methylamino)eth-1-yl)phenyl)benzimidazole-4-carboxamide
12. 2-(4-(2-(Ethylamino)eth-1-yl)phenyl)benzimidazole-4-carboxamide
13. 2-(4-(2-Pyrrolidin-1-yl)eth-1-yl)phenyl)benzimidazole-4-carboxamide
14. 2-(4-(2-(Piperidin-1-yl)eth-1-yl)phenyl)benzimidazole-4-carboxamide
15. 2-(3-(Diethylamino)methyl)phenylbenzimidazole-4-carboxamide
16. 2-(3-(Dimethylamino)methyl)phenylbenzimidazole-4-carboxamide
17. 2-(3-(Pyrrolidin-1-yl)methyl)phenylbenzimidazole-4-carboxamide
18. 2-(3-Piperidin-1-yl)methyl)phenylbenzimidazole-4-carboxamide
19. 2-(3-Aminomethyl)phenylbenzimidazole-4-carboxamide
20. 2-(3-(Methylamino)methyl)phenylbenzimidazole-4-carboxamide
21. 2-(3-(n-Propylamino)methyl)phenylbenzimidazole-4-carboxamide
22. 2-(3-(2-(Diethylamino)eth-1-yl)phenyl)benzimidazole-4-carboxamide
23. 2-(3-(2-(Dimethylamino)eth-1-yl)phenyl)benzimidazole-4-carboxamide
24. 2-(3-(2-Aminoeth-1-yl)phenyl)benzimidazole-4-carboxamide
25. 2-(3-(2-(N-Methylamino)eth-1-yl)phenyl)benzimidazole-4-carboxamide
26. 2-(3-(2-N-Methylamino)eth-1-yl)phenyl)benzimidazole-4-carboxamide
27. 2-(3-(2-(Pyrrolidin-1-yl)eth-1-yl)phenyl)benzimidazole-4-carboxamide
28. 2-(3-(2-(Piperidin-1-yl)eth-1-yl)phenyl)benzimidazole-4-carboxamide
29. 2-(4-N,N-(2-Aminoeth-1-yl)methylamino)phenyl)benzimidazole-4-carboxamide
30. 2-(4-N-(2-(Diethylamino)eth-1-yl)amino)phenyl)benzimidazole-4-carboxamide
31. 2-(4-N-(2-(Dimethylamino)eth-1-yl)amino)phenyl)benzimidazole-4-carboxamide
32. 2-(4-N-(2-Aminoeth-1-yl)amino)phenyl)benzimidazole-4-carboxamide
33. 2-(3-N,N-(2-(Diethylamino)eth-1-yl)methylamino)phenylbenzimidazole-4-carboxamide
34. 2-(3-N,N-(2-Aminoeth-1-yl)methylamino)phenylbenzimidazole-4-carboxamide
35. 2-(3-N-(2-(Diethylamino)eth-1-yl)amino)phenylbenzimidazole-4-carboxamide
36. 2-(3-N-(2-(Diethylamino)eth-1-yl)amino)phenylbenzimidazole-4-carboxamide
37. 2-(3-N-(2-Aminoeth-1-yl)amino)phenylbenzimidazole-4-carboxamide
38. 2-(3-N,N-(d-(Diethylamino)prop-1-yl)methylamino)phenylbenzimidazole-4-carboxamide
39. 2-(3-N,N-(D-(Dimethylamino)prop-1-yl)methylamino)phenylbenzimidazole-4-carboxamide
40. 2-(3-N,N-(3-Aminoprop-1-yl)methylamino)phenylbenzimidazole-4-carboxamide
41. 2-(3-N-(D-(Dimethylamino)prop-1-yl)methylamino)phenylbenzimidazole-4-carboxamide
42. 2-(3-N-(3-(Dimethylamino)prop-1-yl)amion)phenylbenzimidazole-4-carboxamide
43. 2-(3-N-(3-Aminoprop-1-yl)amino)phenylbenzimidazole-4-carboxamide
44. 2-(3-N,N-(2-Pyrrolidion-1-yl-eth-1-yl)methylamino)phenylbenzimidazole-4-carboxamide
45. 2-(3-N-(2-(Pyrrolidion-1-yl)eth-1-yl)amino)phenylbenzimidazole-4-carboxamide
46. 2-(3-N,N-(3-(Pyrrolidin-1-yl)prop-1-yl)methylamino)phenylbenzimidazole-4-carboxamide 47. 2-(3-N,N-(3-(Piperidin-1-yl)prop-1-yl)methylamino)phenylbenzimidazole-4-carboxamide
48. 2-(3-N,N-(2-(Piperidin-1-yl)eth-1-yl)methyamino)phenylbenzimidazole-4-carboxamide Example A Inhibition of the enzyme poly(ADP-ribose) polymerase or PARP (EC 2.4.2.30)

A 96-well microtiter plate (Falcon) is coated with histones (type II-AS; SIGMA H7755). For this, histones are dissolved in carbonate buffer (0.05M NaHCO$_3$; pH 9.4) to give a concentration of 50 µg/ml. The individual wells of the microtiter plate are incubated overnight with 100 µl each of this histone solution. The histone solution is then removed and the individual wells are incubated at room temperature for 2 hours with 200 µl of a 1% strength BSA (bovine serum albumin) solution in carbonate buffer. Washing is then carried out three times with wash buffer (0.05% Tween 10 in PBS). For the enzyme reaction, 50 µl of the enzyme reaction solution (5 µl of reaction buffer (1M tris HCl pH 8.0, 100 mM MgCl$_2$, 10 mM DTT), 0.5 µl of PARP (c=0.22 µg/µl), 4 µl of activated DNA (SIGMA D-4522, 1 mg/ml in water), 40.5 µl of H$_2$O) per well are preincubated for 10 minutes with 10 µl of an inhibitor solution. The enzyme reaction is started by addition of 40 µl of a substrate solution (4 µl of reaction buffer (see above), 8 µl of NAD solution (100 µM in H$_2$O), 28 µl of H$_2$O). The reaction time is 20 minutes at room temperature. The reaction is stopped by washing three times with wash buffer (see above). A one-hour incubation at room temperature with a specific anti-poly-ADP-ribose antibody then follows. The antibody used was a monoclonal anti-poly-(ADP-ribose) antibody "10H"(Kawamaitsu H et al. (1984) Monoclonal antibodies to poly(adenosine diphosphate ribose) recognize different structures. Biochemistry 23, 3771–3777). Polyclonal antibodies can also be used.

The antibodies were employed in a 1:5,000 dilution in antibody buffer (1% BSA in PBS; 0.05% Tween 20). After washing three times with wash buffer, a one-hour incubation at room temperature takes place with the secondary antibody. Here, for the monoclonal antibody, an anti-mouse IgG coupled to peroxidase (Boehringer Mannheim) and for the rabbit antibody an anti-rabbit IgG coupled to peroxidase (SIGMA A-6154), in each case in a 1:10,000 dilution in antibody buffer, were used. After washing three times with wash buffer, the color reaction is carried out using 100 µl/well of color reagent (SIGMA, TMB ready-mix T8540) for about 15 min at room temperature. The color reaction is stopped by addition of 100 µl of 2M H$_2$SO$_4$. It is then immediately measured (450 nm against 620 nm; ELISA plate-reading apparatus "Easy Reader" EAR340AT, SLT Labinstruments, Austria). The IC$_{50}$ value of an inhibitor to be measured is the inhibitor concentration where a half-maximum color concentration change occurs. The K$_i$ value corresponds to the inhibition constant. The following K$_i$ values were determined:

Example 1: 16 nM
Example 2: 10 nM
Example 3: 4 nM

Example B

Determination of the Water Solubility

A compound to be measured is dissolved directly in a specified volume of water and the resulting solution is adjusted to pH 5 to 6 using a sodium acetate solution so that the concentration of the active compound to be tested is achieved. If the measured substance is not present as a water-soluble salt, this was dissolved in as little dimethyl sulfoxide as possible and then diluted with water (final concentration of dimethyl sulfoxide ≦1%), after which the pH was additionally adjusted here too. The potent PARP inhibitor NU 1076 (WO 97/04771) here showed a solubility of <0.01%, compared with which the example according to the invention has a solubility of >0.5%.

Example C

Test of PARP Inhibitors in a Cellular Assay

To test the action of PARP inhibitors, eukaryotic cell lines are treated with chemicals such that the DNA of the cell line is damaged and as a result the PARP enzyme present in the cells is activated. Due to the activation of the enzyme, chains of poly-ADP-ribose (PAR) are formed on proteins. These chains are bound by a specific antibody. This is in turn bound by a second antibody which is provided with a fluorescent label. The fluorescence is measured using a fluorescence scanner and behaves proportionately to the activity of the enzyme PARP. PARP inhibitors can be recognized by a weakening of the fluorescence signal. In order to prevent adulterations of the results by different cell counts, the DNA of the cells is labeled with a further dye and its fluorescence is likewise determined in the fluorescence scanner.

400,000 cells of the human cell line C4I are incubated at 37° C., 5% CO$_2$ with 10% fetal bovine serum in RPMI medium in cell culture plates having 24 cavities until a thick cell lawn is obtained. The cells are washed with DMEM and the PARP inhibitors to be tested are added in various concentrations in DMEM. After incubation for 20 min at 37° C., a concentration of 1 mM is established using hydrogen peroxide and the mixture is incubated at 37° C. for a further 10 min. For the control, cells in some cavities are not treated with hydrogen peroxide (no PARP activation) or receive no inhibitor (maximal PARP activation). The cells are washed once with PBS and fixed at −20° C. for 10 min by addition of methanol/acetone mixture which is precooled to −20° C. (7 parts methanol, 3 parts acetone). The cells are then dried, rehydrated at room temperature for 10 min by addition of PBS, and nonspecific binding sites are blocked for 30 min at room temperature in PBS with 0.05% Tween 20 and 5% dried milk powder. The mouse anti-PAR antibody is added in a concentration of 20 µg/ml in PBS with 0.05% Tween 20 and 5% dried milk powder and the mixture is incubated at 37° C. for 1 h. Unbound antibody is removed by washing 5 times with PBS for 5 min in each case. The mixture is then incubated at 37° C for 30 min with a dilute goat anti-mouse FITC-coupled second antibody (dilution 1:50 in PBS with 0.05% Tween 20, 5% dried milk powder and 1 µg/ml of DAPI (4', 6-diamidino-2-phenylindole)). Unbound antibody is removed by washing 5 times with PBS for 5 min in each case. The FITC and DAPI fluorescence is measured at several sites in the cavities with the aid of a fluorescence scanner. For analysis, the FITC signal is standardized to the DAPI signal. The IC$_{50}$ values are calculated by semilogarithmic plotting of the standardized values of the various inhibitor concentrations. The following IC$_{50}$ values were determined:

Example 1: 115 nM
Example 2: 119 nM
Example 3: 118 nM

We claim:
1. A compound selected from the group consisting of

2-(4-(N,N-2-(N,N-diethylamino)eth-1-ylmethylamino) phenyl)benzimidazole-4-carboxamide,
2-(4-(N,N-2-(N,N-dimethylamino)eth-1-ylmethylamino) phenyl)benzimidazole-4-carboxamide, and
2-(3-(2-(N,N-dimethylamino)eth-1-yl)-4-nitrophenyl) benzimidazole-4-carboxamide,
or a prodrug or salt thereof.

2. A method of preparing a pharmaceutical composition for the treatment of a pathologically increased activity of poly(ATP-ribose)polymerase which comprises admixing an effective amount of a compound of formula I

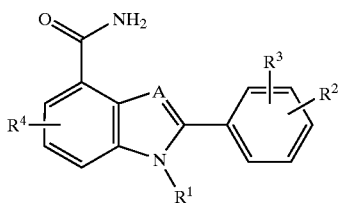

(I)

wherein
A is N or CH,
$R^1$ is hydrogen or $C_1$–$C_6$-alkyl which optionally carries a radical $OR^{11}$,
$R^{11}$ is hydrogen or $C_1$–$C_4$-alkyl,
$R^2$ is hydrogen, chlorine, fluorine, bromine, iodine, $C_1$–$C_6$-alkyl, nitro, $CF_3$, CN, $OR^{21}$, $NR^{21}R^{22}$ or NH—CO—$R^{23}$,
$R^{21}$ and $R^{22}$ are independent from one another and denote hydrogen or $C_1$–$C_4$-alkyl,
$R^{23}$ is hydrogen, $C_1$–$C_4$-alkyl or phenyl,
$R^3$ is $NR^{31}R^{32}$ or $(CH_2)_q$—$NR^{33}R^{34}$,
q is 1, 2 or 3,
$R^{31}$ is hydrogen, $C_1$–$C_6$-alkyl or $(CH_2)_r NR^{33}R^{34}$,
$R^{32}$ is $(CH_2)_r NR^{33}R^{34}$,
r is 2, 3, 4, 5 or 6,
$R^{33}$ and $R^{34}$ are independent from one another and denote hydrogen, $C_1$–$C_6$-alkyl, together with the nitrogen to which they are bonded form a 3 to 8-membered ring formed of the nitrogen atom, carbon ring members and optionally one ring member selected from the group consisting of O, NH, $N(C_1$–$C_4$-alkyl) and $N(C_0$–$C_2$-alkylphenyl), phenyl-$C_1$–$C_4$-alkyl, wherein the phenyl ring is unsubstituted or substituted by 1 to 3 radicals selected from the group consisting of $C_1$–$C_6$-alkyl, halogen, nitro, $SO_2NR^{35}R^{36}$, $C_1$–$C_4$-alkoxy, $S(O)_{0-2}$—$R^{37}$, $CF_3$, $(CH_2)_{0-4}$—$COR^{37}$, $(CH_2)_{0-4}$—$NR^{35}R^{36}$, $(CH_2)_{0-4}$—$CONR^{35}R^{36}$, $(CH_2)_{0-4}$—$OR^{37}$, $(CH_2)_{0-4}$—$CH_2COOR^{37}$,
$R^{35}$ and $R^{36}$ are independent from one another and denote hydrogen or $C_1$–$C_4$-alkyl, or
$R^{35}$ and $R^{36}$ together with the nitrogen to which they are bonded form a 3 to 8-membered ring formed of the nitrogen atom, carbon ring members and optionally one ring member selected from the group consisting of O, S, $SO_2$, NH, $N(C_1$–$C_4$-alkyl) and $N(C_0$–$C_2$-alkylphenyl),
$R^{37}$ is hydrogen or $C_1$–$C_4$-alkyl,
$R^4$ is hydrogen, $C_1$–$C_6$-alkyl, chlorine, bromine, fluorine, nitro, cyano, $OR^{41}$, $NR^{41}R^{42}$ or NH—CO—$R^{43}$,
$R^{41}$ and $R^{42}$ are independent from one another and denote hydrogen or $C_1$–$C_4$-alkyl, and
$R^{43}$ is $C_1$–$C_4$-alkyl or phenyl,
or a tautomeric form, an enantiomeric or diastereomeric form, or a prodrug or a physiologically tolerable salt thereof, with at least one customary pharmaceutical auxiliary.

3. The method of claim 2, wherein $R^2$ is in the 3-position and $R^4$ is in the 4-position, or $R^2$ is in the 4-position and $R^3$ is in the 3-position relative to the benzimidazole ring.

4. The method of claim 2, wherein $R^1$ and $R^4$ are hydrogen.

5. The method of claim 2, wherein $R^2$ is hydrogen, nitro, CN, $NH_2$, $C_1$–$C_6$-alkyl or O—$C_1$–$C_4$-alkyl.

6. The method of claim 2, wherein $R^3$ is —$CH_2$—$NR^{33}R^{34}$, —$(CH_2)_2$—$NR^{33}R^{34}$, —$N(R^{31})$—$(CH_2)_2$—$NR^{33}R^{34}$ or —$N(R^{31})$—$(CH_2)_3$—$NR^{33}R^{34}$, and
$R^{31}$ is hydrogen or $C_1$–$C_4$-alkyl,
$R^{33}$ and $R^{34}$ are independent from one another and denote hydrogen or $C_1$–$C_4$-alkyl, or
$R^{33}$ and $R^{34}$ together with the nitrogen to which they are bonded form a ring selected from the group consisting of piperidine, pyrrolidine, azepine and piperazine, wherein the second nitrogen ring member of the piperazine ring carries hydrogen or a $C_1$–$C_4$-alkyl group.

7. The method of claim 2, wherein $R^2$ is hydrogen and A is nitrogen.

8. The method of claim 7, wherein the pharmaceutical composition is adapted for the treatment of a pathologically increased activity of poly(ATP-ribose)polymerase due to sepsis or multi-organ failure.

9. The method of claim 7, wherein the pharmaceutical composition is adapted for the treatment of a pathologically increased activity of poly(ATP-ribose)polymerase due to diabetes mellitus.

10. The method of claim 2, wherein the pharmaceutical composition is adapted for the treatment of a pathologically increased activity of poly(ATP-ribose)polymerase due to a neurodegenerative disease or neuronal damage.

11. The method of claim 10, wherein the neurodegenerative disease or neuronal damage is due to ischemia, trauma or mass hemorrhages.

12. The method of claim 10, wherein the neurodegenerative disease or neuronal damage is due to a stroke or a craniocerebral trauma.

13. The method of claim 10, wherein the neurodegenerative disease or neuronal damage is due to Alzheimer's disease, Parkinson's disease or Huntington's disease.

14. The method of claim 2, wherein the pharmaceutical composition is adapted for the treatment or prophylaxis of a pathologically increased activity of poly(ATP-ribose) polymerase due to ischemia.

15. The method of claim 2, wherein the pharmaceutical composition is adapted for the treatment of a pathologically increased activity of poly(ATP-ribose)polymerase due to epilepsy.

16. The method of claim 2, wherein the pharmaceutical composition is adapted for the treatment of a pathologically increased activity of poly(ATP-ribose)polymerase due to kidney damage, renal ischemia or kidney transplantation.

17. The method of claim 2, wherein the pharmaceutical composition is adapted for the treatment of a pathologically increased activity of poly(ATP-ribose)polymerase due to damage to the heart after cardiac ischemia.

18. The method of claim 2, wherein the pharmaceutical composition is adapted for the treatment of a pathologically increased activity of poly(ATP-ribose)polymerase due to a microinfract, a heart valve replacement, an aneurysm resection or a heart transplantation.

19. The method of claim 2, wherein the pharmaceutical composition is adapted for the treatment of a pathologically increased activity of poly(ATP-ribose)polymerase in a revascularization of a critically constricted coronary or peripheral artery.

20. The method of claim 2, wherein the pharmaceutical composition is adapted for the treatment of a pathologically increased activity of poly(ATP-ribose)polymerase in an acute myocardial infract, or due to medicinal or mechanical lysis thereof.

21. The method of claim 2, wherein the pharmaceutical composition is adapted for the treatment of a pathologically increased activity of poly(ATP-ribose)polymerase due to a tumor or metastasis of a tumor.

22. The method of claim 2, wherein the pharmaceutical composition is adapted for the treatment of a pathologically increased activity of poly(ATP-ribose)polymerase due to an immunological disease.

* * * * *